(12) United States Patent
Paterlini-Brechot

(10) Patent No.: US 7,651,838 B2
(45) Date of Patent: Jan. 26, 2010

(54) PRENATAL DIAGNOSIS METHOD ON ISOLATED FOETAL CELL OF MATERNAL BLOOD

(75) Inventor: Patrizia Paterlini-Brechot, Paris (FR)

(73) Assignees: Institut National de la Sante et de la Recherche Medicale, Paris (FR); Assistance Publique-Hopitaux de Paris, Paris (FR); Universite Rene Descartes Paris 5, Paris (FR)

( * ) Notice: Subject to any disclaimer, the term of this patent is extended or adjusted under 35 U.S.C. 154(b) by 0 days.

(21) Appl. No.: 10/695,744

(22) Filed: Oct. 30, 2003

(65) Prior Publication Data

US 2005/0049793 A1 Mar. 3, 2005

Related U.S. Application Data

(63) Continuation of application No. PCT/FR02/01505, filed on Apr. 30, 2002.

(30) Foreign Application Priority Data

Apr. 30, 2001 (FR) .................................... 01 05824

(51) Int. Cl.
C12Q 1/68 (2006.01)
C12P 19/34 (2006.01)
G01N 33/53 (2006.01)

(52) U.S. Cl. .............................. 435/6; 435/7.1; 435/7.2; 435/7.21; 435/7.24; 435/7.25; 435/91.1; 435/91.2

(58) Field of Classification Search ........................ None
See application file for complete search history.

(56) References Cited

U.S. PATENT DOCUMENTS

| | | | |
|---|---|---|---|
| 5,306,420 A * | 4/1994 | Bisconte | 210/143 |
| 5,501,954 A | 3/1996 | Mahr et al. | |
| 5,503,981 A | 4/1996 | Mueller et al. | |
| 5,580,724 A | 12/1996 | Alter | |
| 5,641,628 A | 6/1997 | Bianchi | |
| 5,646,004 A | 7/1997 | Van Vlasselaer | |
| 5,714,325 A | 2/1998 | Bianchi | |
| 6,143,577 A | 11/2000 | Bisconte Sconte De Saint Julien | |
| 6,159,685 A * | 12/2000 | Pinkel et al. | 435/6 |
| 6,309,822 B1 * | 10/2001 | Fodor et al. | 435/6 |

2002/0028431 A1 3/2002 Julien

FOREIGN PATENT DOCUMENTS

| | | |
|---|---|---|
| FR | 2 782 730 A1 | 3/2000 |
| WO | WO 90/06509 A1 | 6/1990 |
| WO | WO 97/42503 A1 | 11/1997 |
| WO | WO 99/15892 A1 | 4/1999 |

OTHER PUBLICATIONS

Sterlitech Corporation, via the Internet at <URL: sterlitech.com/products/membranes/polycrabonate/PCTEPProduct.htm> Polycarbonate (PCTE) Membrane Product and Performance Characteristics.*
Whatman Cyclospore Membranes, Jan. 17, 2000, available via url: <cyc.ucl.ac.be/TechApplic/whatman/index.html>.*
Gentaur BVBV- BIOXYS, available via url: <bioxys.com/i_ Whatman/cyclopore_polycarbonate_and_polyester_membranes.htm>.*
Vona et al., American Journal of Pathology, vol. 156, No. 1, 57-63, Jan. 2000.
Bianchi, British Journal of Haematology, 1999, 105, 574-583.
Vona et al., American Journal of Pathology, Vo. 160, No. 1, 51-58, Jan. 2002.
Naro et al., "Prenatal diagnosis of β-thalassaemia using fetal erythroblasts enriched from maternal blood by a novel gradient," Molecular Human Reproduction, vol. 6, No. 6, pp. 571-574, 2000.
Watanabe et al., "Prenatal diagnosis of ornithine transcarbamylase deficiency by using a single nucleated erythrocyte from maternal blood," Hum. Genet., vol. 102, pp. 611-615, 1998.
Sekizawa et al., "Analysis of HLA-DQ α sequences for prenatal diagnosis in single fetal cells from maternal blood," Hum. Genet., vol. 102, pp. 393-396, 1998.

* cited by examiner

*Primary Examiner*—Carla Myers
(74) *Attorney, Agent, or Firm*—Birch, Stewart, Kolasch & Birch, LLP

(57) ABSTRACT

The invention concerns a novel non-invasive prenatal diagnostic method implemented with a sample of maternal blood. Said method enables prenatal diagnosis on isolated non-apoptotic epithelial foetal cells of maternal blood after they have been enriched by filtration, morphologically or immunologically and genetically analysed. Said method is advantageous in that it is perfectly harmless for the mother and the foetus and provides a highly sensitive and specific diagnosis. It enables early detection of a genetic or chromosomal abnormality of the foetus, of a genetic or infectious (viral, bacterial or parasitic) pathology of the foetus, of accurate genotype, and in particular of the genetic sex of the foetus.

18 Claims, 2 Drawing Sheets

PRENATAL DIAGNOSIS METHOD ON ISOLATED FOETAL CELL OF MATERNAL BLOOD

This application is a continuation of PCT International Application No. PCT/FR02/01505, filed Apr. 30, 2002.

The present invention relates to a novel method for non-invasive prenatal diagnosis carried out on a maternal blood sample. Said method allows prenatal diagnosis to be carried out on non-apoptotic epithelial foetal cells isolated from maternal blood after enriching them by filtration, and their morphological or immunological and genetic analysis. Particular advantages of this method are its harmlessness towards the mother or the foetus and the very high sensitivity and specificity of the diagnosis. It allows early detection of a genetic or chromosomal anomaly of the foetus, or a genetic disease or infectious disease (viral, bacterial or parasitic) of the foetus, accurate genotyping, and in particular determination of the genetic sex of the foetus.

Prenatal diagnostic methods are primarily aimed at obtaining genetic information on a foetus or an embryo. The search for genetic information on a foetus consists either of identifying the presence of a specific allele of a given gene or a combination of alleles on a given foetal DNA sequence, or of genetically associating a foetal DNA polymorphism with a particular allele. One major application of prenatal genetic diagnosis concerns the detection of congenital anomalies.

Prenatal genetic diagnostic methods used in clinical practice essentially involve invasive techniques such as amniocentesis, the removal of chorionic villi, the removal of foetal blood or tissue biopsies. Those techniques involve obtaining samples directly from the foetus or indirectly from ovular structures. Because of the highly invasive nature of those methods, they are prone to complications for the mother or the foetus. Examples of such complications which can be cited in the case of amniocentesis are the risk of infection, foeto-maternal haemorrhage with possible allo-immunization, loss of amniotic fluid and abdominal pain. Different studies have estimated the risk of a miscarriage after amniocentesis at 0.2% to 2.1% higher than that of the control group. As a result, amniocentesis is only suggested for women in whom the risk of having a child with a genetic handicap exceeds that of iatrogenic miscarriage.

In order to limit the use of invasive prenatal diagnostic techniques risking the complications mentioned above and which are generally disagreeable and/or the source of stress for the mother, the development of novel non invasive methods constitutes a major aim in modern obstetrics.

In particular, foetal cells circulating in maternal blood constitutes a source of genetic material that is of potential use for prenatal genetic diagnosis (1, 2).

During pregnancy, different cell types of foetal origin traverse the placenta and circulate in the maternal blood (1). Such cell types include lymphoid and erythroid cells, myeloid precursors and trophoblastic epithelial cells (cytotrophoblasts and syncytiotrophoblasts).

Methods for analyzing the genome of foetal cells circulating in maternal blood with a view to prenatal diagnosis have been described in the prior art, but they remain relatively limited as regards sensitivity and the specificity of the diagnosis (3, 4, 5, 6). The advantage in developing a non invasive, highly specific prenatal diagnosis method results from the possibility of using it to reduce the proportion of invasive diagnostic methods carried out in pregnant women for whom the result is negative in the end. By way of example, in the case of trisomy 21, which concerns one woman in 700, prenatal diagnosis is currently offered in France only if the mother is 38 years old, while a biochemical analytical test capable of detecting 60% of trisomy 21s for 5% of the price of amniocentesis is proposed for younger women. However, 40% of trisomy 21 cases are not detected by currently available tests. Prenatal detection of trisomy 21 in foetal cells isolated from the maternal plasma using a FISH technique has recently been described. That approach is interesting, but as foetal cells are rare in plasma (1 in 500 to 1 in 2000) and often include apoptotic cells, reliable diagnosis would require carrying out the method on a very large number of cells, rendering it impossible to carry out routinely. Further, euploid foetal cells cannot be identified by that approach.

One limitation of such approaches derives from the fact that foetal cells circulating in the blood are present in very low concentrations. Studies based on PCR detection of the Y chromosome in blood samples without prior selection have allowed the mean number of foetal cells to be determined to be about 1 cell per milliliter of blood (7). Further, it has been shown that foetal cells of myeloid or lymphoid origin (CD34 or CD38 positive) are still present in maternal blood up to 27 years after pregnancy or miscarriage (8). When isolating them, then, it is not certain that they derive from the current pregnancy. Thus, it is easy to imagine technical difficulties with developing prenatal diagnosis of maternal blood that can be routinely used and with the need to concentrate epithelial foetal cells (trophoblasts) which are destroyed after each pregnancy and which allow an analysis of the foetal genome for the current pregnancy.

Several authors, however, have proposed the improvement to the sensitivity of detection of foetal cells in maternal blood by enriching the cell population contained in maternal blood in foetal cells or by separating foetal cells contained in maternal blood (see review 1, 2).

In particular, the prior art discloses methods for separating circulating foetal cells based on their affinities for certain antibodies.

As an example, International patent application WO-A-97/42503 (BIOCOM S A) describes a method for magnetic immunoseparation of foetal cells, consisting of fixing foetal cells on paramagnetic beads onto antibodies directed against antigens expressed on the surface of the foetal cells which have been fixed. WO-A-90/06509 (Finders Technologies Pty, Ltd) describes a method for isolating trophoblastic cells for prenatal diagnosis using an antibody recognizing antigens expressed on the surface of trophoblastic cells. However, no antibody that is exclusively specific for foetal cells has currently been found. This point is important, as prenatal diagnosis must be carried out on a "pure" foetal cell population.

Examples of methods for enriching a cell population derived from maternal blood in foetal cells that can be cited are U.S. Pat. No. 5,714,325 (New England Medical Center Hospitals), U.S. Pat. No. 5,580,724 (Board of Regents, The University of Texas System), and U.S. Pat. No. 5,646,004 (Activated Cell Therapy, Inc).

U.S. Pat. No. 5,714,325 describes a method for enriching foetal granulocytes by separating foetal granulocytes from maternal cells using an antibody that recognizes antigens expressed on the surface of foetal granulocytes, in particular using a combination of an anti-CD71 antibody (transferrin receptor) and an antiglycophorin A antibody.

U.S. Pat. No. 5,580,724 describes a further method for enriching foetal cells in a cell population derived from maternal blood by in vitro stimulation of foetal cell proliferation using specific growth factors.

Foetal cells can also be enriched by centrifuging a blood sample in a solution with a gradient density (PERCOLL, FICOLL, albumin, sucrose or dextran, for example) as described in U.S. Pat. No. 5,646,004.

However, it has been shown that those protocols include a plurality of isolation steps that may damage the foetal cells and give rise to significant cell loss. Further, none of those methods can enrich the cell population from maternal cell in foetal cells to a sufficient extent to envisage routine specific sensitive prenatal diagnosis. The sensitivity of a diagnosis carried out on foetal cells (and hence its reliability) is directly correlated with the purity of the preparations of foetal cells used for diagnosis. None of the enriching methods cited above can produce non apoptotic and sufficiently pure foetal cells, in particular those not free of cells of maternal origin.

As a result, there is a genuine need to develop novel methods for non invasive diagnosis with a sensitivity and diagnostic specificity that is very high, preferably close to 100%.

In view of the prior art and the nature of the foetal cells circulating in maternal blood, the invention results from the fact that only one method allowing sufficient concentration of foetal cells, associated with their morphological examination and genetic analysis targeted to the genome of single cells, can overcome the disadvantages of existing methods.

A method for separating pathogenic epithelial cells circulating in the blood, in particular tumour cells, by filtering a sample of a biological liquid has been described in French patent application FR-A-2 782 730. It is based on the fact that circulating epithelial cells are bigger than leukocyte cells. Vona et al (9) have used that filtration method to detect and identify different cancerous cell lines mixed in very small concentrations in a blood sample (1 to 3 cells per milliliter of blood) as well as tumour cells isolated from patients with liver cancer.

The inventors have now discovered that it is possible to combine the method for filtering cells described by Vona et al, the immunological or cytological analysis of cells retained by filtering and a genetic analysis method targeted to individual cells to obtain sufficient enrichment of cells of foetal origin to carry out prenatal diagnosis on the genome of individual foetal cells isolated from maternal blood and the foetal origin of which has been clearly demonstrated. In particular, the present invention can enrich a population of cells derived from maternal blood in epithelial foetal cells by a factor of more than six million. The method of the invention can detect 1 to 7 foetal cells per 2 ml of maternal blood being analyzed. Thus, it can thus be concluded that the method of the invention can isolate almost all of the foetal cells present in maternal blood. Further, after filtering and collecting cells by microdissection, the inventors have shown that it is possible to observe two characteristic cell types, one being mononucleated of cytotrophoblastic type with a diameter in the range about 14 to 20 μm and the other plurinucleated, syncytiotrophoblastic in type, with a diameter of about 44-47 μm or more.

One study carried out on 13 women 11-12 weeks into pregnancy showed that it was possible to diagnose the masculine sex of the foetus by analyzing 2 milliliters of maternal blood via the detection of specific sequences on the Y chromosome in the genome of single microdissected cells. It has also been shown that it is possible to determine, by allelotyping, the foetal or maternal origin of these isolated cells.

The present invention flows in part from the discovery that foetal cells can be concentrated by carrying out a filtration method as described in FR-A-2 782 730. The invention also flows in part from the demonstration that morphological analysis of cells retained on the filter can establish a presumption regarding the foetal or maternal origin of said cells and their genetic analysis can demonstrate their foetal or maternal origin. In particular, it shows that prenatal diagnosis can be carried out on a pure foetal genome obtained by microdissection of single cells. Finally, the invention flows from the demonstration that the prenatal diagnostic method can be carried out at an early stage of pregnancy and using a limited volume of sampled maternal blood.

The term "prenatal diagnosis" means both the identification of a particular characteristic of the foetus (for example the sex) or the identification of a genetic anomaly or any type of genetic pathology (DNA alteration), infectious disease (viral, bacterial or parasitic) or metabolic disease (alteration to the synthesis of messenger RNA and/or proteins) which can be detected from a genetic analysis of isolated foetal cells.

Thus, depending on the selected implementations of the invention, prenatal diagnosis consists of identifying a genetic anomaly or chromosomal anomaly on the DNA of a foetal cell, a genetic or infectious disease (viral, bacterial or parasitic) or identifying a precise genotype; in particular the genetic sex of the foetus.

The term "slightly invasive or non invasive method" means a method that does not involve the removal of tissues or foetal cells by biopsy and/or effraction from the placentary barrier.

Thus, the invention provides a method for prenatal diagnosis of foetal cells isolated from maternal blood comprising the following steps:
a) filtering a sample of pure or diluted maternal blood to concentrate on a filter, according to size, certain circulating cells and in particular cells of foetal origin;
b) analyzing the cells retained on the filter to obtain a presumption or an identification of their foetal or maternal origin; and identifying their epithelial nature;
c) demonstrating the foetal origin of certain enriched cells by genetic analysis of individually isolated cells;
d) identifying genetic anomalies specifically targeted to individually analyzed cellular genomes for which a foetal origin has been demonstrated.

In order to be reliable, prenatal diagnosis must be carried out on a pure foetal genome. The term "presumption" or "presumed" in step b) thus indicates the high probability of being in the presence of a cell of foetal origin.

During step c), the analysis is preferably carried out by genetic analysis using specific markers for foetal genomes, as will be explained in more detail below.

The characteristic(s) of foetal cells that can be identified in step d) can be either a genetic anomaly or a chromosomic anomaly of the foetus, or a particular genotype of the latter.

This particular characteristic is preferably sought by genetic analysis of single cells the foetal origin of which has already been demonstrated.

The prenatal diagnosis of the invention requires that a blood sample be removed from the pregnant woman. In one particular implementation of the invention, a sample of maternal blood is removed early on in pregnancy (for example at about the fifth week of pregnancy). However, removing the sample of maternal blood and the diagnostic method of the invention can be carried out at any time from the start to the end of pregnancy. In a preferred implementation of the invention, sampling and the diagnostic method are carried out between the $7^{th}$ and $15^{th}$ week of pregnancy. In a further implementation, sampling and the diagnostic method are carried out between the $10^{th}$ and $15^{th}$ week of pregnancy. In general, between 3 and 20 milliliters of maternal blood are removed, preferably between 5 and 10 milliliters. If for practical reasons between 3 and 20 ml of maternal blood are removed, it should be understood that subsequent analysis of foetal cells isolated as will be described below can be carried out on a more limited volume of the blood sample, for example in the range 1 to 10 ml, preferably in the range 2 to 5 ml. In order to increase the sensitivity of the diagnosis, it is possible to take a plurality of independent samples to repeat the diagnosis on different independent samples. Further, in a preferred implementation of the invention, it is possible to remove a blood sample from the father at the same time, and a cell sample from the mother, for example by removing buccal cells by "scraping" or blood prior to pregnancy, and to use the sampled material to identify specific markers of the paternal and maternal genome. This parallel study allows specific genetic markers of the father and mother to be determined, which markers could be used to demonstrate the foetal origin of cells isolated by filtering depending on the implementation described below.

The invention results from the observation that the diameter of epithelial cells circulating in the blood is higher than maternal leukocyte or erythrocyte cells and can be isolated using filtration methods that are adapted to those described for the isolation of pathogenic cells circulating in the blood, such as those described in French patent FR-A-2 782 730.

In accordance with the method of the invention, the blood sample is filtered to concentrate on the filter, depending on size, certain circulating cells of foetal or maternal origin and to then separate them from sanguine cells, in particular maternal leukocytes.

Prior to the filtration step a), any method that can enrich the cell population from the blood sample in cells of foetal origin can be carried out. In one implementation of the invention, the foetal cell population is enriched by sorting the cells as a function of the expression of surface markers expressed by the foetal cells to reduce the proportion of cells of maternal origin. Examples of cell sorting techniques are FACS, immunoaffinity column separation or immunomagnetic separation (MACS) or any technique that is capable of obtaining enrichment of one cell type on the basis of physical characteristics (density) or structural characteristics (in particular specific antigens).

In order to facilitate filtering, in one particular implementation, prior to the filtration step, the blood sample is diluted in a filtration solution, said filtration solution consisting of a reagent for fixing nucleated cells and/or for lysing red blood cells. One example of a filtration solution comprises a detergent capable of degrading the red blood cell membrane, such as saponin, and a fixing agent that is capable of stabilizing the membrane of nucleated cells, such as formaldehyde.

In a preferred implementation, the sample of maternal blood is diluted about 10 to 100-fold in the filtration solution.

The pure or diluted maternal blood sample is filtered using a porous filter that can separate cells according to size. The pore size of the filter is selected to allow the blood elements, in particular erythrocytes, platelets and maternal leukocytes, to pass through and to retain certain nucleated cells, in particular large cells (epithelial cells or haematopoietic precursors) of maternal or foetal origin.

Advantageously, the filter used has a pore size of between 6 and 15 µm and a density that is adapted to the selected pore size and which can retain cells while avoiding blockage thereof during filtration. Preferably, the filter has substantially cylindrical pores with a diameter of about 8 µm and a density in the range $5 \times 10^4$ to $5 \times 10^5$ pores/cm$^2$. More preferably, the filter used is graded so that all of the pores have a substantially identical diameter. One example of a filter that can be used in the method of the invention is a polycarbonate graded filtration membrane of the "Track-Etched Membrane" type with a pore density of $1 \times 10^5$ pores/cm$^2$, a thickness of 12 µm and a pore size of 8 µm, such as that sold by Whatman®.

The cells retained on the filter can be observed under a microscope, for example after staining with hematoxylin and eosin to analyze their morphology. Their epithelial nature can be identified, for example, by immunolabelling with an anti-cytokeratin antibody (type $KL_1$). It is at this stage possible to envisage recognizing, on the basis of morphological characteristics, the cells of foetal origin and in particular cytotrophoblastic, mononucleated cells with a large nucleus, a condensed chromatin and a reduced cytoplasm, with a diameter in the range 14 to 20 µm, and syncytiotrophoblastic cells with a larger diameter (44-47 µm or more) and plurinucleated.

The genetic analysis of cells retained on the filter can produce indications of the foetal or maternal origin of each of said cells. In particular, with a view to a sensitive and specific diagnosis, the filtration step will be repeated if no cell presumed to be of foetal origin is observed on the filter after a first filtration. Depending on the implementations, genetic analysis can be carried out for all of the cells retained on the filter and comprising certain cells the foetal origin of which is presumed, or on the genome of individually isolated cells.

In one particular implementation, the presumption of the foetal or maternal origin of cells retained on the filter is analyzed by identifying the presence of immunological or cytological marker(s) that are characteristic of foetal cells.

The term "characteristic immunological marker of foetal cells" means any antigen or combination of antigens the expression of which is significantly different between foetal and maternal cells, and which can be detected using an antibody or a combination of antibodies directed specifically against said antigen or combination of antigens. Particular examples of said immunological markers are antigens associated with trophoblastic cells described in WO-A-90/06509. Identifying the presence of immunological markers that are characteristic of foetal cells consists, for example:

of bringing cells contained in the maternal blood sample into contact with at least one antibody directed against an antigen characteristic of foetal cells; and of determining, on cells retained on the filter, a specific binding of said antibody with an antigen expressed on the surface of said cells; said contact of cells with the antibody possibly being carried out before or after a filtration step. The selected antibodies can be of a polyclonal or monoclonal type.

One example of an antigen that is characteristic of foetal cells is the antigen of placental alkaline phosphatase.

In a further implementation, the presumption of the foetal origin of cells can be analyzed by determining specific cytological markers of cytotrophoblastic and/or syncytiotrophoblastic cells. Cytological markers that can be used includes all the cytological characteristics s of foetal cells that allow them to be differentiated from other circulating cell types that may be retained on the filter, in particular cell size, cell shape, the presence and size of particular organites, the size and number of nuclei, the chromatin structure, etc. . . . , or any particular combinations of said cytological characteristics. The cytological characteristics can be observed by staining the cells using stains that are conventionally used in cytology, in particular haematoxylin-eosin and by observing the stained cells under an optical microscope.

When identifying a chromosomal anomaly or the sex of a foetus, in one particular implementation, in situ hybridization of probes specific to the chromosomal anomaly or the sex to be detected, on the genome of cells retained on the filter, and the identification of specific hybridization of the genome of cells the foetal origin of which is presumed. Specific probes for a chromosomal sequence can be DNA or PNA (peptide nucleic acid) type probes (11). One example of an in situ hybridization technique is known as FISH (Fluorescence In Situ Hybridization) (10), but any method that is known to the skilled person that can detect a chromosomal anomaly or sex chromosomes on the genome of a cell using specific probes can be used in the context of the invention.

Examples of detectable chromosomal anomalies that can be cited are trisomy 13, trisomy 18, trisomy 21, Turner's syndrome, Penta X syndrome, XYY syndrome and Klinefelter's syndrome.

In a further particularly preferred implementation of the invention, after analyzing the presumption of the foetal or maternal origin of cells, the cells the foetal origin of which is presumed are individually collected. The term "individual collection of cells" should be understood to mean any method that can collect an individual specific cell retained on the filter for its subsequent analysis independently of the other cells retained on the filter. In a preferred implementation, cells retained on the filter are collected individually by microdissection. Individual collection of a cell by microdissection consists of laser cutting the portion of the filtration membrane on which a cell is retained or detaching the cell from the filter using a laser then recovering the single cell collected in a suitable tube. This can then undergo different analyses allowing prenatal diagnosis as described in more detail below.

The individual collection of cells can advantageously target the genetic analysis to the genome of a single cell. It also allows identification of a genetic or chromosomal anomaly of the foetus or a particular genotype thereof on the genome of a single cell the foetal origin of which has already been demonstrated by genetic analysis. Using this implementation of the invention, then, we advantageously obtain pure genetic material, i.e., derived from a single cell, and which can be used both to demonstrate the foetal origin of the cell under analysis then for any identification of a genetic anomaly or a characteristic thereof, or a particular genotype.

Any type of genetic analysis method can be used to demonstrate the foetal or maternal origin of a single collected cell or to proceed to identify genetic anomalies of the foetus or a particular genotype thereof provided that said methods are sufficiently sensitive to identify those characteristics in a single cell.

One preferred method of analysis to demonstrate foetal origin is DNA allelotyping of the collected cells, in particular by identifying specific microsatellite markers of paternal or maternal DNA.

As a result, it is possible to:
demonstrate the foetal or maternal origin of cells; then
carry out prenatal diagnosis by identifying genetic anomalies or chromosomal anomalies of the foetus or a particular genotype thereof;
by identification, on a DNA preparation derived from a single collected cell, of one or more genetic markers/target(s) or of the polymorphisim or a combination of said markers/targets, or by a particular allelic assay of said markers or of a genetic target.

In the text below, we prefer the term "genetic target" to refer to the genetic characteristic to be identified, including polymorphism, in the context of prenatal diagnosis and the term "marker" to refer to elements that can demonstrate the foetal or maternal origin of the analyzed cells.

The term "genetic target" means any genetic characteristic, for example a particular mutation of a gene, specifically associated with a phenotype or a genetic disease or infectious disease of the foetus.

The term "polymorphism marker" means any characteristic that can be identified in DNA the presence of which is correlated with a particular genotype. These markers can distinguish paternal DNA from maternal DNA and thus can demonstrate the bi-parental composition of foetal DNA. Examples of markers that can be cited are restriction fragment length polymorphism (RFLP) markers, SNP (Single Nucleotide Polymorphism) markers, microsatellite markers, VNTR (Variable Number of Tandem Repeats) markers or STR (Short Tandem Repeats) markers.

Microsatellite markers are particularly preferred for the characterization of cells and for implementing prenatal diagnosis. In one implementation of the invention, at least one marker for polymorphism to be identified is a microsatellite marker, a VNTR (Variable Number of Tandem Repeats) marker or a STR (Short Tandem Repeats) marker. These have the advantage of being identifiable by amplification using specific primers. Microsatellite markers, VNTR or STR, are composed of tandem repeats, usually polyCA/GT moieties. Allelic variations, due to a variation in the number of repeats, are readily detected by PCR type amplification using primers corresponding to the unique sequences flanking the microsatellite. A physical map of these microsatellite markers and the sequence of their associated primers have been described by Dib et al (12). Using this methodology, a bi-parental contribution of the genotype of the analyzed cells can establish in a definite manner the foetal origin of the cells being analyzed. Further, the presence of particular microsatellite markers can be specifically researched, in particular as a genetic target, for prenatal diagnosis, in particular for the diagnosis of particular chromosomal changes.

To demonstrate the foetal or maternal origin of a single collected cell, in one particular implementation, a marker or a combination of markers or an allelic assay of said markers distinguished from those of the maternal cell genome can be identified, in particular by identifying, on the genome of said collected cell, a marker or a combination of markers specific to the DNA of paternal cells. Their presence is necessarily a signature of the foetal origin of the cell in question.

When the sex of the foetus is known to be male, one specific marker for the DNA of foetal cells may be a genetic marker specific for the Y chromosome or a combination of said markers.

Advantageously, prior to demonstrating the foetal or maternal origin of a collected cell and/or seeking a genetic or chromosomal anomaly of the foetus or a particular genotype thereof, said collected cell is lysed and its entire genome is pre-amplified, for example using generic primers covering all possible sequences using known PEP (Primer Extension Preamplification) methods (13) or using the DOP-PCR method. Such methods can amplify the whole genome of a single cell. The preamplified DNA preparation obtained and derived from the DNA of a single cell can then be purified and used as genetic material for the specific detection of genetic markers or of polymorphism and/or for detecting a genetic target.

Preferably, the foetal or maternal origin of a collected cell is demonstrated by amplification of genetic markers or polymorphism or a combination of said markers, from the preamplified DNA preparation derived from the DNA of a single cell. The genetic markers that are capable of demonstrating the bi-parental contribution to foetal DNA are identified by prior analysis of paternal and maternal DNA. It is then possible to identify a genetic target for prenatal diagnosis from the same preamplified DNA preparation derived from the DNA of a single cell by amplifying one or more sequence(s) carrying the identified genetic target(s). Any technique for specific amplification of a given nucleic acid can be used in the method of the invention. Examples that can be cited are the PCR amplification (Polymerase Chain Reaction) or isothermal amplification methods such as TMA (Transcription Mediated Amplification), NASBA (nucleic acid sequence based amplification), 3SR (Self Sustained Sequence Replication) or Strand Displacement Amplification.

Amplification methods, in particular PCR, are sufficiently sensitive to be implemented from less than one fifth of the preamplified DNA preparation. As a result, each preamplified DNA preparation of a collected cell can be used to amplify at least five different markers or genetic targets.

In particular, the amplifications carried out can detect microsatellite markers. By way of illustration, for example, we can cite the detection of microsatellite markers to demonstrate the foetal origin of cells isolated using the method of the invention using the PCR amplification of the preamplified DNA preparations. PCR amplification can also detect genetic targets, in particular point mutations or deletion type mutations or microdeletions associated with a genetic nature or with a specific disease. The sequences that are susceptible of carrying the deletion are amplified and the amplification products are separated according to size, for example by electrophoresis. The presence of deletions is detected by the presence of an amplification product that is smaller than amplification products carrying no deletions.

The amplification products can also be sequenced, in particular to accurately characterize the identified markers or genetic targets and in particular mutations or genotypes identified with a view to prenatal diagnosis. In one particular implementation, we can demonstrate the foetal or maternal origin of a collected cell and/or prenatal diagnosis, in particular seeking a genetic or chromosomal anomaly of the foetus or a particular genotype thereof by sequencing the amplified markers or genetic targets. As an example, it is possible to detect using the method of the invention certain mutations of the CFTR gene associated with diagnosing cystic fibrosis such as the $\Delta F$ 508 microdeletion of the CFTR gene.

It is also possible to diagnose trisomy 21 by PCR amplification of VNTR markers of chromosome 21 such as the D21S1414 and D21S1411 markers and allelic assay of said markers.

In a further implementation of the method of the invention, we can demonstrate the foetal or maternal origin of an individually collected cell then carry out prenatal diagnosis in particular when seeking a genetic or chromosomal anomaly of the foetus or a particular genotype thereof by hybridizing all or a portion of the preamplified DNA preparation using specific DNA probes. The DNA probes are selected so that they hybridize specifically to genetic targets or polymorphisms for their identification, or to sequences carrying the genetic target(s) to be identified. Hybridization of the probes to the genetic targets can be detected using conventional techniques for detecting hybridization complexes of nucleic acids of the slot blot, Southern blot or advantageously now using DNA micro- or macro-arrays (14). Molecular probes can, for example, be selected for the specific detection of cystic fibrosis, muscular dystrophies, Gaucher's disease, haemoglobinopathies, haemophilia, penylketonurias and cystic fibrosis.

In one implementation of the invention, DNA probes specific for genetic targets, to be identified are fixed to a support forming a DNA micro- or macro-array. The preamplified DNA preparation is, for example, labeled with a radioactive or fluorescent marker and brought into contact with the DNA micro- or macro-array comprising the specific probes. The hybdridization intensity is measured for each spot containing a specific probe, thus providing great sensitivity of determination of the presence of the desired markers on the DNA of a collected cell.

The choice of genetic targets clearly depends on the genotype to be sought. Examples of genetic targets that can be used for prenatal diagnosis are described in the prior art.

An alternative method for determining chromosomal anomalies and in particular gains and losses of chromosomes for prenatal diagnosis is the comparative genomic hybridization method (CGH) consisting (i) of comparing hybridization on a chromosomal or cosmid preparation or on a DNA array, preparing pre-amplified DNA derived from the genome of a single cell collected after filtration in accordance with the method, and preparing pre-amplified DNA from cells of maternal origin or non foetal reference cells, the two preparations having been labeled with different markers, and (ii) identifying differences in hybridization between the DNA of the collected cell after filtration and maternal DNA (16). In one implementation of the invention, prenatal diagnosis is carried out by means of comparative genomic hybridization (CGH) of a preamplified DNA preparation derived from the DNA of a single collected cell and for which its foetal origin has been demonstrated, and of a preamplified DNA preparation of cells of maternal origin or of non foetal reference cells.

In a further aspect, the invention concerns a method for producing a population of foetal cells derived from a population of cells isolated from maternal blood and concentrated in cells of foetal origin, said method comprising the following steps:
a) filtering a sample of pure or diluted blood removed from a pregnant woman to concentrate, on a filter according to size, certain circulating cells and in particular cells of foetal origin; and
b) culturing the cells retained on the filter to obtain a cell culture concentrated in foetal cells.

The method described above results from the observation by the inventors that, unexpectedly, the method of the invention can particularly significantly concentrate a population of cells isolated from maternal blood in cells of foetal origin. It also results from the observation that the cells can be filtered even without prior fixing, i.e. with retained viability.

Further, from populations of cells obtained by the above method, it is possible to obtain pure cultures of foetal cells using known cloning and expansion techniques. The pure or enriched foetal cell populations obtained by the method have particular applications in preparing a cell therapy product comprising said foetal cells or cells derived from their differentiation.

The methods described above are based on the existence and development, of a specific apparatus for Isolation by Size of Epithelial Tumour Cells, ISET, described in European patent EP-A-0 513 139 and comprising, on a frame:
a porous filter that can retain certain circulating cells according to their size, mounted between two clamping devices respectively upstream and downstream with respect to the filtration direction, and providing a filtration seal;
the upstream block comprising means for storing and/or pre-treating of the samples to be analyzed;
the downstream block comprising perforations facing the storing means to collect waste;
means for forced filtration.

The invention pertains to the adaptation and use of an apparatus of said type to filtering foetal cells present in maternal blood.

The term "adaptation and use" means:
incorporating into the apparatus a filter with a pore size that is preferably graded and can retain cells with a mean diameter of more than 8 µm, preferably more than 10 µm and more preferably more than 15 µm. A filter with s mean pore size of 8 µm has been shown to satisfy the desired characteristics;

adapting the pore density of the filter as a function of the pore size to optimize the filtration capacity;

adapting the pressure applied to the filtration means to retain the physical integrity of the foetal cells;

adapting the diluting medium for the maternal blood sample to conserve the integrity and viability of the subject cells.

More particularly, the invention pertains to the use of an ISET type filtration apparatus to isolate foetal cells from maternal blood and comprising a filter with a mean pore size in the range 6 µm to 15 µm, preferably about 8 µm.

It also pertains to the use of an ISET type apparatus in which the filter has pores with a diameter of about 8 µm and a pore density in the range $5 \times 10^4$ to $5 \times 10^5$.

Finally, it pertains to the use of an ISET type filtration device in which the filtration pressure applied is in the range 0.05 bars to 0.8 bars, preferably about 0.1 bars.

The examples below and the accompanying Figures illustrate an implementation of the prenatal diagnosis method and its application to detecting foetal sex. They also demonstrate its sensitivity and specificity.

More precisely, in the example below, the diagnostic method was carried out on cells isolated from 13 pregnant women. The method used comprised detecting foetal cells by morphological analysis and specific markers for the male sex (amplification primers for sequences of the Y chromosome). They also included demonstrating the foetal origin of cells retained on the filter by allelotyping of microsatellite markers using PCR amplification. The results show that the diagnostic method is particular sensitive since in mothers carrying female foetuses, 100% of the cells were negative to the Y chromosome test. Further, analyzing specific microsatellite markers (STR, short tandem repeats) on 11 isolated cells revealed that 6 thereof had a "foetal cell" type profile and 5 had a "maternal" profile. These results are in agreement with the results obtained for Y chromosome detection. They constitute molecular proof that the test can allow specific detection of foetal cells and the implementation of a particular sensitive and specific prenatal diagnosis.

Clearly, this example is not limiting and the method of the invention is applicable to prenatal diagnosis of any foetal characteristic provided that it can be identified from an isolated foetal cell, individualized and characterized, using the means described above.

Figure 1:
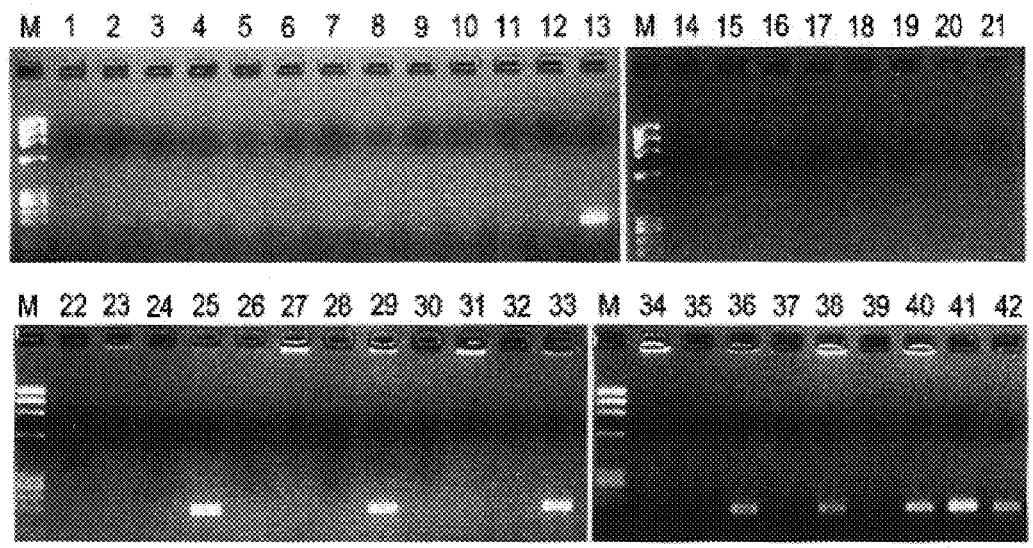
FIG. 1: polyacrylamide gel of PCR amplification products carried out on trophoblast cells obtained by the method of the invention. The different points numbered 1 to 42 represent the following.

Tracks 1 to 21: Y primer specifity test by amplification of DNA obtained from 20 women (tracks 1 to 12 and 14 to 21) and one man (track 13, positive control). The test was negative for the samples of DNA from the women and positive for the DNA from the man.

Tracks 22 to 42: PCR test of Y primers on individual cells isolated from the blood of a mother carrying a male foetus (tracks 23, 25, 27, 29, 31, 33, 34, 36 and 38).

The Y primer test was positive for the DNA of male foetal cells in tracks 25, 29, 33, 36 and 38.

The Y primer test was negative for the DNA from maternal cells, tracks 23, 27, 31 and 34.

Tracks 22, 24, 26, 28, 30, 32, 35, 37 and 39: Result of negative controls corresponding to the buffer with no sample inserted in the cell lysis step and continued until the end of the test.

Tracks 41 and 42: Result of positive controls: a HuH6 cell (track 40), 5 ng and 2 ng of DNA derived from leukocytes from blood of 3 men (tracks 41 and 42).

M: molecular weight marker (digested ΦX174 HaeIII).

Figure 2A:
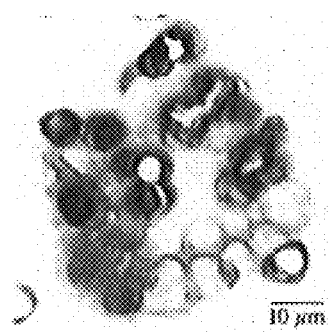
Figure 2B:
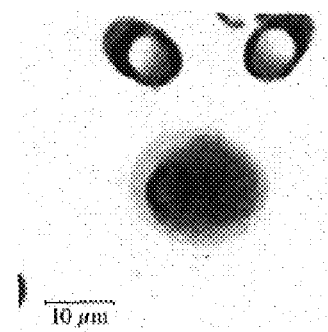

FIG. 2: Microscopic analysis of morphological characteristics of circulating foetal cells isolated by ISET.

A: polynucleated syncytiotrophoblastic cells.

B: mononucleated cells with a cytotrophoblast morphology observed on a filter.

Two empty pores can be seen at the top of the photograph.

Figure 3:
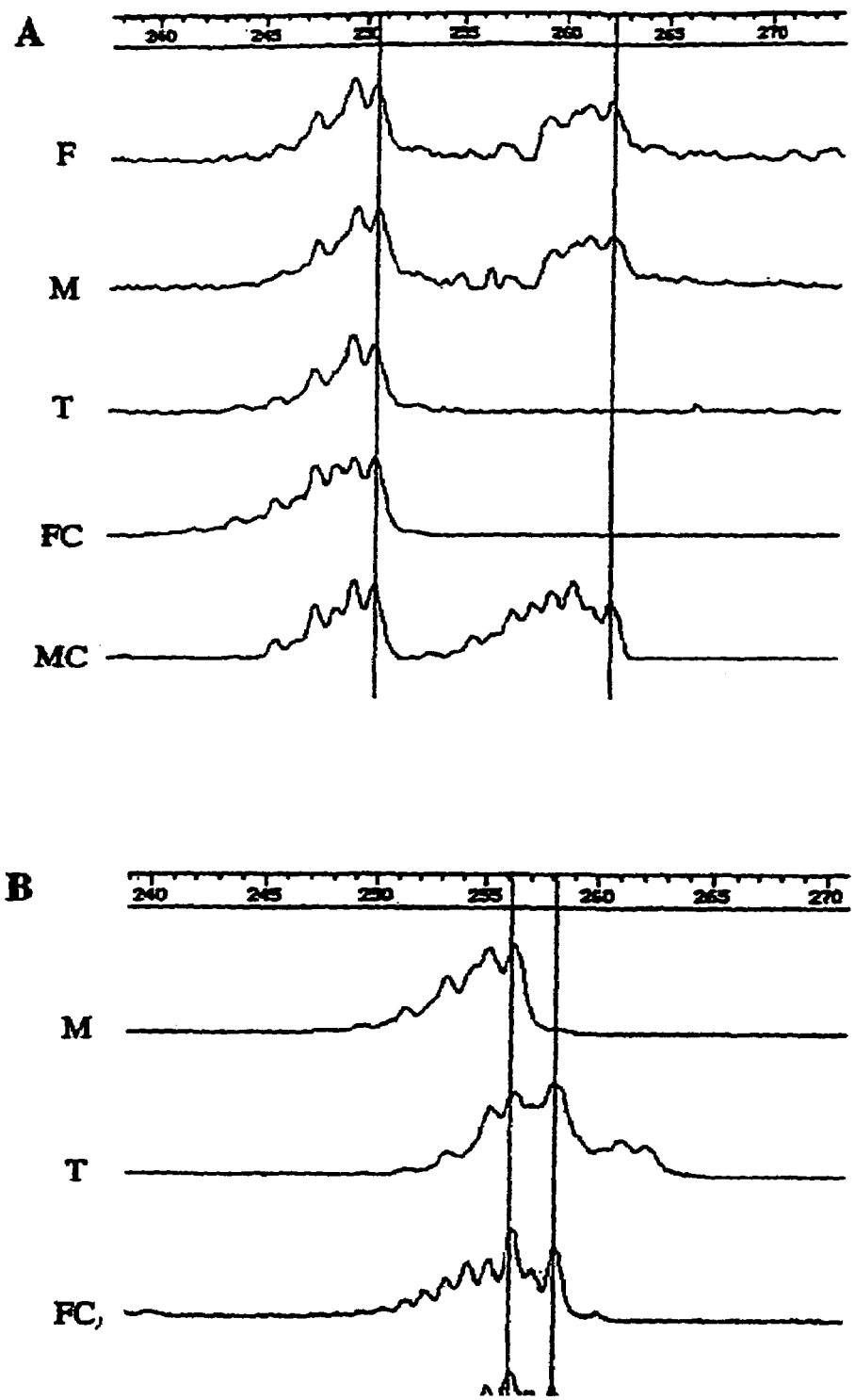

FIG. 3: Genotyping using STR markers of parental and trophoblast DNA and DNA from cells isolated from maternal blood and collected individually after filtration.

The electrophoretograms of the amplified products obtained using specific markers for the STR marker (Short Tandem Repeat) D1653018 are shown.

A: The STR marker used in this case could not distinguish the maternal (M) or paternal (F) origin of the DNA (heterozygotic state, alleles 250 bp and 262 bp). However, trophoblastic DNA (T) exhibited a homozygotic state for one allele (250 bp) and an identical profile was found for a foetal cell (FC). In contrast, another microdissected cell (maternal cell, MC) had a clearly maternal profile (heterozygotic state).

B: In this example, the STR marker could distinguish the paternal or maternal origin of the cells. Trophoblastic DNA (T) had a 256 bp allele, also found in the maternal DNA (M); in contrast, the paternal DNA had a different 258 bp allele. The two alleles, 256 bp and 258 bp, were detected on two microdissected cells, thus demonstrating their foetal origin (FC).

EXAMPLE OF IMPLEMENTATION OF PRENATAL DIAGNOSTIC METHOD ON FOETAL CELLS ISOLATED FROM MATERNAL BLOOD

Application to Determination of the Foetus Sex

Summary of Study

The study was carried out on 13 women at 11 to 12 weeks pregnancy carrying a foetus with a risk of genetic disease (6 male foetuses and 7 female foetuses) and recruited with their consent. Two milliliters of blood removed and recovered in a EDTA buffer were analyzed. Sampling was carried out prior to any invasive protocols and the blood sample was filtered at most 4 hours after removal. The diagnosis of the foetal sex (by DNA analysis) was established by removing chorionic villi.

A. Methods

The blood samples were diluted 10 fold in a filtration buffer containing 0.175% of saponin, 0.2% of paraformaldehyde, 0.0372% of EDTA and 0.1% of BSA, then filtered using a graded polycarbonate filter with cylindrical graded pores 8 µm in diameter. The cells retained on the filter were collected on a circular spot 0.6 cm in diameter. After staining with eosin and hematoxylin, the spots were analyzed under a microscope and a photograph of each cell was taken at high and low magnification. The cell size was determined using Adobe Photoshop software taking the 8 µm pore size as the reference. The photographs allowed the cells to be located with a Pixcell II Arcturus microscope (Mountain View, Calif.). FIG. 2 shows the microscopic analysis obtained by this method.

Microdissection of each cell was carried out by laser capture without any prior treatment of the filter. In order to ensure that a single cell was collected each time, photographs of the filter were taken before and after microdissection and of the microdissected cell deposited on the capsule (CapSure™ HS). The cell was then lysed in 15 μl of lysis buffer (100 mM Tris-HCl pH 8, 400 μg/ml proteinase K) for 16 hours at 37° C. The lysate was collected after centrifuging and the proteinase K was deactivated at 90° C. for 10 minutes. After primer extension preamplification (PEP) as described by Zhang et al (see above), the DNA was precipitated in ethanol and resuspended in 10 μl of water. Each sample was then tested, firstly with the following HLA primers:

```
5'-GTGCTGCAGGTGTAAACTTGTACCAG-3';
(SEQ ID NO:1)

5'-CACGGATCCGGTAGCAGCGGTAGAGTT-3';
(SEQ ID NO:2)
``` the HLA primers could test the amplification ability of the DNA (positive amplification control), and secondly with the following STR-specific primers:

```
Marker D16S3018
(sense)
5'-6-FAM-GGATAAACATAGAGCGACAGTTC-3'; and
(SEQ ID NO:3)

(antisense)
5'-AGACAGAGTCCCAGGCATT-3';
(SEQ ID NO:4)

Marker D16S3031
(sense)
5'-TET-ACTTACCACTGTGCCAGTTG-3'; and
(SEQ ID NO:5)

(antisense)
5'-ATACATGGGTCCTTAAACCG-3';
(SEQ ID NO:6)

Marker D16S539
(sense)
5'-HEX-GATCCCAAGCTCTTCCTCTT-3'; and
(SEQ ID NO:7)

(antisense)
5'-ACGTTTGTGTGTGCATCTGT-3'.
(SEQ ID NO:8)
```

The samples were also tested with specific primers for the Y chromosome (Y primers: Y1.7 and Y1.9 as described in reference 17). PCR was carried out in a reaction mixture volume of 20 μl containing 2 μl of PEP product, 10 mM of tris-HCl, 50 mM of KCl, 1.5 mM of MgCl$_2$, 0.01% of gelatin, 200 mM of each deoxynucleotide, 20 picomoles of each Y primer, HLA or STR and 1 U of Taq polymerase (Perkin-Elmer Cetus, Emeryville, Calif.). After an initial denaturing step at 94° C. for 5 minutes, 40 amplification cycles (94° C., 15 s, 60° C. 30 s, 72° C. 30 s) were carried out then a final elongation step at 72° C. for 5 minutes in a Perkin Elmer 9700 Thermocycler. 10 μl aliquots of the amplification products were analyzed by gel electrophoresis on 2% agarose.

The results are shown in FIG. 1. The PCR conditions for amplification using specific primers for the Y chromosome were established by amplification of 5 ng of DNA derived from blood leukocytes of 3 male individuals then by amplification of the pre-amplified DNA product of HuH6 cells (derived from a hepatocellular carcinoma), filtered and microdissected. For PCR using STR-specific primers, after denaturing the DNA at 94° C. for 5 minutes, 40 amplification cycles were carried out (94° C., 30"; 54° C. 30"; 72° C., 20") followed by an elongation phase at 72° C. for 5 minutes. Two microliters of the first PCR product were re-amplified using the same PCR conditions. One microliter of the final PCR product was mixed with 20 μl of deionized formamide and 0.4 μl of Genescan-500 TAMRA marker then loaded into an ABI Prism 310 automatic sequencer. The profiles were analyzed using Genescan software (Perkin Elmer, Foster City, Calif.). Allelotyping was carried out by amplification, using the same STR primers, of 1.5 ng of paternal DNA derived from blood leukocytes and/or 1.5 ng of maternal DNA derived from maternal blood or leukocytes prior to pregnancy and 1.5 ng of trophoblastic DNA obtained from a sample from chorionic villi.

Specificity Control

The specificity of Y primers was tested by amplification of 10 ng of DNA derived from the blood leukocytes from 20 women. The precautions employed to avoid any contamination of PCR products have been described above (18). Further, a negative control (the buffer without a sample) was intercalated for each sample into the lysis step and analyzed like the other samples until the end of the test. When carrying out the microdissection, we included at least one microdissection of a new filter (without cells) which was carried out in parallel with the samples and controls. Amplification was repeated with the specific Y chromosome primers or the STR-specific primers for the samples and controls, negative and positive, to verify the specificity of the positive results.

B. Results

The specificity of Y primers in amplifying the DNA obtained from 20 women was determined. The test was negative for DNA samples from women and positive for DNA from a man as a positive control, as shown in FIG. 1 by comparing tracks 1 to 12, 14 to 21 (women) and line 13 (man).

A preliminary test was then carried out on blood from a mother carrying a male foetus. The cells retained on the filter were microdissected and analyzed using the specific primers for the Y chromosome and HLA defined in section A. The test with the HLA primers was positive for all cells and the test with Y primers was positive for half of those cells.

FIG. 2 illustrates the fact that on cells that were positive in the test, the photographs taken of said cells on the filter revealed two cell types with the following morphological characteristics:

mononucleated cells of the cytotrophoblast type with a diameter in the range 14.3 to 19.9 μm (mean value 16.9±2), a large nucleus with condensed chromatin and little cytoplasm, often with several microvilli on the membrane surface;

polynucleated cells, of the syncytiotrophoblast type with a larger diameter (generally about 44-47 μm).

Twenty-three cells of "foetal" morphological appearance derived from blood samples from a woman carrying a male foetus and twenty-six cells deriving from a female foetus were then analyzed by microdissection and amplification of Y chromosome sequences. The results are shown in Table 1 below.

TABLE 1

| Mothers | Collected cells | Y positive cells | Mononucleated cells (Y positive) | Polynucleated cells (Y positive) |
|---|---|---|---|---|
| Male foetus | | | | |
| 1 | 2 | 2 | 1 (1) | 1 (1) |
| 2 | 3 | 2 | 3 (2) | 0 |
| 3 | 8 | 7 | 6 (5) | 2 (2) |

TABLE 1-continued

| Mothers | Collected cells | Y positive cells | Mononucleated cells (Y positive) | Polynucleated cells (Y positive) |
|---|---|---|---|---|
| 4 | 2 | 1 | 2 (1) | 0 |
| 5 | 3 | 1 | 3 (1) | 0 |
| 6 | 5 | 2 | 5 (2) | 0 |
| Total Female foetus | 23 | 15 | 20 (12) | 3 (3) |
| 7 | 6 | 0 | 6 | 0 |
| 8 | 3 | 0 | 1 | 2 |
| 9 | 3 | 0 | 2 | 1 |
| 10 | 2 | 0 | 1 | 1 |
| 11 | 6 | 0 | 5 | 1 |
| 12 | 3 | 0 | 3 | 0 |
| 13 | 3 | 0 | 2 | 1 |
| Total | 26 | 0 | 20 | 6 |

The number of Y positive cells is shown in brackets.

This table shows that the test with HLA primers was positive for all cells and the test with Y primers was positive for 15 cells.

To test the specificity of these results, the Y amplification products were reamplified with the same Y primers. All of the controls and the cells negative to PCR gave a negative result in the test, while positive cells gave a positive result, and a weakly positive cell (track 34 in FIG. 1) produced a stronger band.

Overall, determination of cells of foetal origin was proved for a varying number of cells (from 1 to 7 Y positive cells) isolated from 2 ml of blood. However, in this study, not all the cells with a "foetal" morphological appearance were microdissected. Based on the morphological data, a first rapid estimation gave their number at about 5 cells per milliliter of blood.

The second part of the table indicates results for the analysis of female foetal cells. It can be seen that the test using HLA primers was positive for the 26 cells being analyzed derived from a female foetus, while the test using Y chromosome-specific primers was negative for all of the cells derived from a female foetus. These results show that this approach can specifically detect foetal cells with no false positives, and can be suitable for determining gender.

In four cases, paternal blood DNA and/or maternal blood DNA (obtained prior to pregnancy) and trophoblastic DNA were available. These DNA samples were used to identify the foetal origin of cells isolated independently of gender identification. By using three STR markers and a fifth of the preamplified DNA preparation, it was possible to determine the foetal or maternal origin of 11 microdissected cells isolated from a mother carrying a male foetus and also tested using Y chromosome-specific primers. The results are summarized in Table 2 and in FIG. 3.

TABLE 2

| | | | Genotyping of single collected cell | | |
|---|---|---|---|---|---|
| Mother n°* | Single collected cell | V specific PCR | Marker D16S539 | Marker D16S3018 | Marker D16S3031 |
| 2 | 2a | + | FC | | |
|  | 2b | + | FC | | |
| 3 | 3a | + | | FC | |
|  | 3b | + | | FC | |
|  | 3c | − | | | MC |
|  | 3d | + | | | FC |

TABLE 2-continued

| | | | Genotyping of single collected cell | | |
|---|---|---|---|---|---|
| Mother n°* | Single collected cell | V specific PCR | Marker D16S539 | Marker D16S3018 | Marker D16S3031 |
| 4 | 4a | − | | MC | |
|  | 4b | + | | FC | |
| 6 | 6a | − | | | MC |
|  | 6b | − | | | MC |
|  | 6c | − | | | MC |

*See Table 1; MC: maternal cell; FC: foetal cell profile.

STR Genotyping of Single Cells Isolated from Maternal Blood and Collected Individually after Filtration Six cells had a foetal profile that agreed with positive Y chromosome detection and 5 cells had a maternal profile, in agreement with negative detection of the Y chromosome.

In one case (FIG. 3A), the tested STR markers could not distinguish paternal alleles (F) from maternal alleles (M) (heterozygotic, 250 and 262 bp), however trophoblastic DNA (T) had a homozygotic state for one allele (250 bp). The same profile (homozygotic for the 250 bp allele) was detected for a foetal cell (FC) isolated using the method of the invention, which cell was positive to the Y chromosome detection test. In contrast, a further microdissected cell, negative to the Y chromosome detection test, had a clearly heterozygotic profile (maternal cell, MC).

In another case (FIG. 3B), in addition to the maternal allele (256 bp) also detected in maternal DNA (M), trophoblastic DNA (T) also had a paternal allele (258 bp). These two alleles were found on both microdissected cells (FC), determining their foetal origin.

Discussion

This study shows for the first time that it is possible to concentrate foetal cells circulating in maternal blood by filtration. It also shows that identification of foetal cells independently of the identification of sex, can be carried out, by PCR amplification of highly polymorphic STR markers. The clinical impact of the STR marker detection method depends on the possibility of combining said method with a particularly effective approach for enriching foetal cells. This study shows for the first time that it is possible to successfully combine the two approaches. The size separation technique has already been described for separating tumour cells circulating in the blood (Vona et al, see above). The inventors have now discovered that it is possible to concentrate and genetically analyze foetal cells collected after their concentration, from only two milliliters of a sample of maternal blood. In combination with laser microdissection and PCR on an individual cell using Y chromosome specific primers or STR primers, this approach has allowed the foetal origin of collected cells to be demonstrated. Considering that the number of foetal cells circulating in the blood is estimated to be one cell per milliliter of blood, i.e. one foetal cell per 10 million leukocytes, the enrichment obtained is a factor of about 6.6 million (one foetal cell per 1.5 large cells retained on the filter). Further, this approach can provide morphological information on foetal cells circulating in the blood. Mononucleated cells, which are probably cytotrophoblast type cells, and polynucleated cells which are syncytiotrophoblastic cells, have been isolated. These two cell types were never observed in 22 healthy blood donors and 44 patients with carcinomas analyzed using the same separation and microdissection technique (results not shown).

Further, foetal lymphoid or myeloid progenitors persist in the blood after pregnancy, but not trophoblastic cells. The advantage of an analysis of trophoblastic cells is thus that it can positively associate the results of a genetic test with a current pregnancy.

A further advantage of this approach is the possibility of carrying out at least 5 PCR analyses from the DNA of a single individual cell. This gives the possibility of carrying out a genetic test on cells the foetal origin of which will have been proved in parallel with molecular analysis, in particular by STR polymorphic marker analysis. It is also possible to base the diagnosis on the confrontation of independent results obtained for different individual foetal cells isolated from repeated blood samples. Importantly, it should be noted that the FISH protocol can also be successfully applied to cells isolated using the filtration method (9). The other advantages of the method of the invention reside firstly in its sensitivity since almost 100% of foetal cells, collected on the basis of their morphological observation and analyzed, are identified as such by the method of the invention, and by its specificity since apoptotic foetal cells and cells of maternal origin in particular can be removed from the analysis in view of their genetic and morphological characteristics.

The method of the invention thus provides a novel approach for carrying out early, non-invasive and particularly sensitive and specific prenatal diagnosis.

REFERENCES

1. Bianchi, D. Fetal cells in the maternal circulation: feasibility for prenatal diagnosis. *Br J Haematol* 1999 105: 574-583
2. Fisk N. Maternal-fetal medicine and prenatal diagnosis. *Currt Opin Obstet Gynecol* 1998 10: 81-83
3. Di Naro E, Ghezzi F, Vitucci A, et al. Prenatal diagnosis of β-thalassemia using fetal erythroblasts enriched from maternal blood by a novel gradient. *Mol Hum Reprod* 2000 6: 571-574
4. Watanabe A, Sekizawa A, Taguchi A, et al. Prenatal diagnosis of ornithine transcarbamylase deficiency by using a single nucleated erythrocyte from maternal blood. *Hum Genet* 1998 102: 611-615
5. Takabayashi H, Kuwabara S, Ukita T, Ikawa K, Yamafuji K, Igarashi T. Development of non-invasive fetal DNA diagnosis from maternal blood. *Prenat Diagn* 1995 15: 74-77
6. Sekizawa A, Taguchi A, Watanabe A, et al. Analysis of HLA-DQ alpha sequences for prenatal diagnosis in single fetal cells from maternal blood. *Hum Genet* 1998 102: 393-396
7. Bianchi D W. Current knowledge about fetal blood cells in the maternal circulation. *J Perinat Med* 1998 26: 175-85
8. Bianchi D W et al., PNAS 1996, 93: 705
9. Vona G, Sabile A, Louha M, et al. Isolation by Size of Epithelial Tumor cells. A new method for the immunomorphological and molecular characterization of circulating tumor cells. *Am J Pathol* 2000 156:57-63.
10. Poon L L, Leung T N, Lau T K, Lo Y M. Presence of fetal RNA in maternal plasma [In Process Citation]. *Clin Chem* 2000; 46(11):1832-4.
11. Lohse, J., Dahl O., Nielsen P E, PNAS 1999 96: 11804-11808. Double duplex invasion by peptide nucleic acid: a general principle for sequence-specific targeting of double-stranded DNA
12. Dib, C., Faure, S., Fizames, C., Samson, D., Drouot, N., Vigna!, A., Missasseau, P., Marc, S., Hazan, J., Seboun, E., Lathrop, M., Gyapay, G., Morissette, J., and Weissenbach, J. A comprehensive genetic map of the human genome based on 5.264 microsatelites. *Nature* 1996 380: 152-154
13. Zhang, L., Cui, X., Schmitt, K., Hubert, R. W N., Amheim, M. Whole genomic amplification from a single cell: implications for genetic analysis. *PNAS* 1992 89: 5847-5851
14. Sambrook et al. Molecular Cloning: A laboratory Manual. 2001 3rd Ed., Cold Spring Harbor Laboratory Press, Cold Spring Harbor, N.Y.
15. Diagnostics prénatals et biologie moléculaire, F. Forestier & D F Schroderet, 1997 Ed. T ec et Doc Lavoisier.
16. Voullaire L, Wilton L, Slater H and Williamson R. Prenat Diagn 1999 19: 846-851
17. Lo Y M, Patel P; Sampietro M, Gillmer M D, Fleming K A, Wainscoat J S. Detection of single-copy fetal DNA sequence from maternal blood [letter]. *Lancet* 1990; 335: 1463-4.
18. Paterlini P, Gerken G, Nakajima E, et al. Polymerase chain reaction to detect hepatitis B virus DNA and RNA sequences in primary liver cancers from patients negative for hepatitis B surface antigen. *N Engl J Med* 1009; 323: 80-85.

The invention claimed is:

1. A method for prenatal diagnosis of foetal cells isolated from maternal blood, comprising the following steps:
   a) diluting a sample of maternal blood collected from a pregnant woman between the $5^{th}$ and $15^{th}$ week of pregnancy in a filtration solution comprising a reagent for fixing nucleated cells and/or a reagent for lysing red blood cells,
   b) filtering said diluted sample of maternal blood, on a filter, which has a pore size of 8 µm and a pore density in the range of $5 \times 10^4$ to $5 \times 10^5$ pores/cm$^2$, and under an applied filtration pressure, said filtration pressure being in the range of 0.05 to 0.8 bars, whereby epithelial cells are retained onto said filter;
   c) analyzing the cells retained on the filter for the presence of at least one immunological or cytological marker, which is characteristic of trophoblastic and/or syncytiotrophoblastic cells, to identify trophoblastic and/or syncytiotrophoblastic cells; and individually collecting at least one cell, which has been identified as being a trophoblastic and/or syncytiotrophoblastic cell, whereby a single cell, which is presumed to be of foetal origin, or a collection of single cells, which are presumed to be of foetal origin, is obtained;
   d) lysing the single cell of step c), or a single cell of the collection obtained at step c), whereby the genome of this single cell is made accessible to amplification primers,
   e) amplifying the genome of the lysed single cell obtained at step d), whereby a pre-amplification product is obtained from a single cell,
   f) using the pre-amplification product obtained at step e), both to demonstrate the foetal origin of the single cell, and to carry out the prenatal diagnosis, wherein:
      i) said pre-amplification product is analyzed for the presence of genetic or polymorphism marker(s), which can, or the allelotyping of which can, be distinguished from the one(s) of a maternal cell genome, by amplification of said marker(s) from said pre-amplification product, whereby said presence demonstrates the foetal origin of said single cell, and
      ii) if said foetal origin is demonstrated, identifying at least one genetic or chromosomal anomaly of the foetus, or a genotype thereof, by genetic analysis of said pre-amplification product.

2. The method of claim 1, wherein the cells retained on the filter are collected individually by microdissection.

3. The method of claim 2, wherein said microdissection consists of laser cutting the portion of the filter on which a cell is retained then recovering the single collected cell in a suitable tube.

4. The method of claim 1, wherein said identifying at least one genetic or chromosomal anomaly of the foetus, or of a genotype thereof, is carried out by identifying one or more genetic target(s) in said preamplification product.

5. The method of claim 4, wherein said at least one genetic or chromosomal anomaly of the foetus, or said genotype thereof, is identified by amplification of one or more sequence(s) carrying the genetic target(s), from said preamplification product.

6. The method of claim 5, wherein said amplification of one or more sequence(s) carrying the genetic target(s) is carried out from less than one fifth of said preamplification product.

7. The method of claim 5, wherein said identifying at least one genetic or chromosomal anomaly of a foetus, or of said genotype thereof, is demonstrated by sequencing the genetic target(s) carried in the amplified sequence(s).

8. The method of claim 1, wherein the foetal origin is demonstrated by identifying a marker or a combination of markers, the presence of which, or the allelotyping of which, is specific to the DNA of paternal cells.

9. The method of claim 1, wherein the filtered maternal blood is derived from a blood sample made after the fifth week of pregnancy.

10. The method of claim 1, wherein prior to dilution, said sample of maternal blood is a sample of 1 to 10 mL of maternal blood.

11. The method of claim 1, wherein the maternal blood sample is diluted 10 to 100 fold in said filtration solution.

12. The method of claim 1, wherein the filter is a polycarbonate filtration membrane, and all of the pores of said polycarbonate filtration membrane have a substantially identical diameter.

13. The method of claim 1, wherein said filter has a pore density of $1 \times 10^5$ pores/cm$^2$ and a thickness of 12 µm.

14. The method of claim 1, wherein prior to step f), the preamplification product of step e) is purified to obtain a preparation of preamplified DNA derived from the genome of said single cell.

15. The method of claim 14, wherein said at least one genetic or chromosomal anomaly of the foetus, or said genotype thereof, is identified by hybridization of all or a portion of the preamplified DNA preparation with specific DNA probes or Peptide Nucleic Acid (PNA) type probes.

16. The method of claim 15, wherein the specific DNA probes are fixed on a support forming a DNA micro- or macro-array.

17. The method of any one of claims 4 or 5-16, 14, wherein at least one of said polymorphism markers is a microsatellite marker, a Variable Number of Tandem Repeats (VNTR) marker, a Single Nucleotide Polymorphism (SNP) marker or a Short Tandem Repeat (STR) marker.

18. The method of claim 14, wherein a chromosomal anomaly is identified by a method for comparative genomic hybridization (CGH) of:
   said preparation of preamplified DNA derived from the genome of said single cell, the foetal origin of which has been demonstrated, and of
   a preamplified DNA preparation of cells of maternal origin or of non foetal reference cells.

* * * * *

SEQUENCE LISTING

<160> NUMBER OF SEQ ID NOS: 8

<210> SEQ ID NO 1
<211> LENGTH: 26
<212> TYPE: DNA
<213> ORGANISM: Artificial Sequence
<220> FEATURE:
<223> OTHER INFORMATION: HLA synthetic primer

<400> SEQUENCE: 1
gtgctgcagg tgtaaacttg taccag                                      26

<210> SEQ ID NO 2
<211> LENGTH: 27
<212> TYPE: DNA
<213> ORGANISM: Artificial Sequence
<220> FEATURE:
<223> OTHER INFORMATION: HLA synthetic primer -continued

```
<400> SEQUENCE: 2
cacggatccg gtagcagcgg tagagtt                                              27

<210> SEQ ID NO 3
<211> LENGTH: 23
<212> TYPE: DNA
<213> ORGANISM: Artificial Sequence
<220> FEATURE:
<223> OTHER INFORMATION: STR synthetic primer

<400> SEQUENCE: 3
ggataaacat agagcgacag ttc                                                  23

<210> SEQ ID NO 4
<211> LENGTH: 19
<212> TYPE: DNA
<213> ORGANISM: Artificial Sequence
<220> FEATURE:
<223> OTHER INFORMATION: STR synthetic primer

<400> SEQUENCE: 4
agacagagtc ccaggcatt                                                       19

<210> SEQ ID NO 5
<211> LENGTH: 20
<212> TYPE: DNA
<213> ORGANISM: Artificial Sequence
<220> FEATURE:
<223> OTHER INFORMATION: STR synthetic primer

<400> SEQUENCE: 5
acttaccact gtgccagttg                                                      20

<210> SEQ ID NO 6
<211> LENGTH: 20
<212> TYPE: DNA
<213> ORGANISM: Artificial Sequence
<220> FEATURE:
<223> OTHER INFORMATION: STR synthetic primer

<400> SEQUENCE: 6
atacatgggt ccttaaaccg                                                      20

<210> SEQ ID NO 7
<211> LENGTH: 20
<212> TYPE: DNA
<213> ORGANISM: Artificial Sequence
<220> FEATURE:
<223> OTHER INFORMATION: STR synthetic primer

<400> SEQUENCE: 7
gatcccaagc tcttcctctt                                                      20

<210> SEQ ID NO 8
<211> LENGTH: 20
<212> TYPE: DNA
<213> ORGANISM: Artificial Sequence
<220> FEATURE:
<223> OTHER INFORMATION: STR synthetic primer

<400> SEQUENCE: 8
acgtttgtgt gtgcatctgt                                                      20
```